United States Patent
Matsubara et al.

(10) Patent No.: US 10,335,336 B2
(45) Date of Patent: *Jul. 2, 2019

(54) INCUBATOR

(71) Applicant: Atom Medical Corporation, Tokyo (JP)

(72) Inventors: Kazuo Matsubara, Tokyo (JP); Terumi Matsubara, Tokyo (JP); Masato Honda, Saitama (JP); Yutaka Sekiguchi, Saitama (JP); Keisuke Wakabayashi, Saitama (JP)

(73) Assignee: Atom Medical Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/039,104

(22) PCT Filed: Aug. 18, 2015

(86) PCT No.: PCT/JP2015/073115
§ 371 (c)(1),
(2) Date: May 25, 2016

(87) PCT Pub. No.: WO2016/067714
PCT Pub. Date: May 6, 2016

(65) Prior Publication Data
US 2017/0224568 A1    Aug. 10, 2017

(30) Foreign Application Priority Data
Oct. 31, 2014 (JP) ................................. 2014-222716

(51) Int. Cl.
*A61G 11/00* (2006.01)
*A61B 6/04* (2006.01)
(Continued)

(52) U.S. Cl.
CPC .......... *A61G 11/006* (2013.01); *A61B 6/0428* (2013.01); *A61B 6/4283* (2013.01);
(Continued)

(58) Field of Classification Search
CPC .............. A61G 11/006; A61G 2210/90; A61B 6/0428; A61B 6/4283; A61F 2007/0088; A61N 2005/0659; A61N 5/0625
See application file for complete search history.

(56) References Cited

U.S. PATENT DOCUMENTS 6,457,196 B1    10/2002  Dykes et al.
10,064,775 B2*   9/2018  Matsubara ........... A61G 11/006
(Continued)

FOREIGN PATENT DOCUMENTS

CN         2508697 Y     11/2002
CN       101428637 A      5/2009
(Continued)

OTHER PUBLICATIONS

Office Action in CN Application No. 201580002571.1, dated Apr. 19, 2017.
(Continued)

*Primary Examiner* — Christine H Matthews
(74) *Attorney, Agent, or Firm* — Hunton Andrews Kurth LLP

(57) ABSTRACT

An incubator having a cassette tray accommodation space which allows for a cassette tray to be readily stored in or taken out of the space through one of a plurality of tray loading or unloading ports. The cassette tray accommodation space includes at least two of the following: a front tray loading or unloading port, a rear tray loading or unloading port, a left tray loading or unloading port, and a right tray loading or unloading port.

10 Claims, 8 Drawing Sheets

(51) Int. Cl.
*A61B 6/00* (2006.01)
*A61F 7/00* (2006.01)
*A61N 5/06* (2006.01)

(52) U.S. Cl.
CPC .............. *A61F 7/00* (2013.01); *A61G 11/00* (2013.01); *A61N 5/0625* (2013.01); *A61F 2007/0088* (2013.01); *A61G 2210/50* (2013.01); *A61G 2210/90* (2013.01); *A61N 2005/0659* (2013.01)

(56) References Cited

U.S. PATENT DOCUMENTS

| | | |
|---|---|---|
| 2003/0153805 A1 | 8/2003 | Felix et al. |
| 2010/0286471 A1* | 11/2010 | Matsubara ............. A61G 11/00 600/22 |
| 2012/0269568 A1 | 10/2012 | Matsubara et al. |
| 2016/0158085 A1* | 6/2016 | Matsubara ........... A61G 11/006 600/22 |

FOREIGN PATENT DOCUMENTS

| | | |
|---|---|---|
| CN | 202445473 U | 2/2012 |
| JP | 4317617 | 8/2009 |
| JP | 2012-223320 | 11/2012 |
| JP | 2014-33769 | 2/2014 |
| RU | 2039544 | 7/1995 |
| WO | 9912510 | 3/1999 |

OTHER PUBLICATIONS

Extended European Search Report issued in EP Application No. 15851640.1 dated Apr. 24, 2017.
Office Action dated Jun. 14, 2017, in corresponding South Korean Application No. 10-2016-7000325.
Office Action issued in Chinese Application No. 201580002571.1 dated Dec. 5, 2017.
International Search Report dated Oct. 6, 2015 in International Application No. PCT/JP2015/073115.
Russia Patent Office Decision to Grant dated Jul. 18, 2018.

* cited by examiner

INCUBATOR

TECHNICAL FIELD

The present invention relates to an incubator including a cassette tray accommodation space which is formed between an incubator base and a bed base and includes a tray loading/unloading port.

BACKGROUND ART

The incubator having the above arrangement has been conventionally known as disclosed in Japanese Patent Laid-Open No. 09-206345. In the incubator (to be referred to as "the incubator in the above patent reference" hereinafter) disclosed in Japanese Patent Laid-Open No. 09-206345, a tray loading/unloading port is provided on the front side of a cassette tray accommodation space formed between an incubator base and a bed base.

Patent Reference: Japanese Patent Laid-Open No. 09-206345

With the incubator in the above patent reference, however, the tray loading/unloading port is provided only on the front side of the cassette tray accommodation space. Therefore, when a doctor or nurse performs an operation such as medical treatment in a region including the front side of the cassette tray accommodation space and its vicinity, it is impossible to store or take out a cassette tray in or from the cassette tray accommodation space unless he/she leaves the region including the front side of the cassette tray accommodation space and its vicinity. In addition, if a sophisticated article such as a sophisticated medical apparatus exists in a region, outside the cassette tray accommodation space, including the front side of the cassette tray accommodation space and its vicinity, it is necessary to move the sophisticated article to another position or change the position or orientation of the incubator.

The present invention effectively solves the above problem in the incubator in the above patent reference with a relatively simple arrangement.

DISCLOSURE OF INVENTION

The present invention relates to an incubator including a cassette tray accommodation space which is formed between an incubator base and a bed base and includes a tray loading/unloading port, characterized in that the cassette tray accommodation space includes at least two tray loading/unloading ports of a front tray loading/unloading port, a rear tray loading/unloading port, a left tray loading/unloading port, and a right tray loading/unloading port. According to the present invention, tray loading/unloading ports are respectively provided on at least two of the front, rear, left, and right sides of the cassette tray accommodation space. Consequently, even if a doctor or nurse performs an operation in a region including the first or second tray loading/unloading port and its vicinity in a region including the cassette tray accommodation space and its vicinity, it is possible to readily store or take out the cassette tray in or from the cassette tray accommodation space through the second or first tray loading/unloading port. Furthermore, even if a sophisticated article such as a sophisticated medical apparatus exists in the region including the first or second tray loading/unloading port and its vicinity in the region including the cassette tray accommodation space and its vicinity, it is possible to readily store or take out the cassette tray in or from the cassette tray accommodation space through the second or first tray loading/unloading port.

According to the first aspect, the present invention is preferably configured such that the incubator comprises a front baby guard, a rear baby guard, a left baby guard, and a right baby guard, wherein one end portion of each of at least two movable baby guards of the four baby guards is pivotably attached to the incubator base, the at least two tray loading/unloading ports are closed by the at least two movable baby guards, respectively, in a backward pivoting state in which each of the at least two movable baby guards is in a substantially erect position, and the at least two tray loading/unloading ports corresponding to the at least two movable baby guards are opened when each of the at least two movable baby guards pivots forward in a substantially hanging direction. According to the first aspect, it is possible to more satisfactorily obtain the above-described effect obtained according to the present invention.

According to the second aspect, the present invention is preferably configured such that the at least two tray loading/unloading ports are the front tray loading/unloading port, the left tray loading/unloading port, and the right tray loading/unloading port. According to the second aspect, it is possible to readily arrange parts such as a strut and infrared heater on the substantially rear side of the incubator base, and manufacture an incubator with a relatively simple arrangement at a relatively low cost, as compared with a case in which a rear tray loading/unloading port is provided.

According to the third aspect, the present invention is preferably configured such that the cassette tray accommodation space includes at least three tray loading/unloading ports of the front tray loading/unloading port, the rear tray loading/unloading port, the left tray loading/unloading port, and the right tray loading/unloading port, four strut portions for supporting the bed base are further included, the four strut portions are a front left first strut portion, a front right second strut portion, a rear left third strut portion, and a rear right fourth strut portion, at least one of a set of the first strut portion and the second strut portion and a set of the third strut portion and the fourth strut portion functions as a position holding portion serving also as a guide portion for a cassette tray when inserting the cassette tray to the cassette tray accommodation space in a back-and-forth direction of the cassette tray accommodation space, and at least one of a set of the first strut portion and the third strut portion and a set of the second strut portion and the fourth strut portion functions as a position holding portion serving also as a guide portion for the cassette tray when inserting the cassette tray to the cassette tray accommodation space in a right-and-left direction of the cassette tray accommodation space. According to the third aspect, when inserting the cassette tray to the cassette tray accommodation space, at least some (in other words, a plurality of) strut portions of the four strut portions for supporting the bed base on the incubator base function as a position holding portion serving also as a guide portion for the cassette tray. Therefore, with a relatively simple structure, it is possible to relatively reliably and relatively simply insert the cassette tray to the cassette tray accommodation space and hold the position of the cassette tray in the cassette tray accommodation space.

According to the fourth aspect, the present invention is preferably configured such that a width of the cassette tray is substantially equal to each of an interval between the first strut portion and the second strut portion, an interval between the first strut portion and the third strut portion, and an interval between the second strut portion and the fourth strut portion. According to the fourth aspect, it is possible to relatively simply and relatively accurately insert or pull out the cassette tray to or from the cassette tray accommodation space along the substantially longitudinal direction of the cassette tray. According to the fifth aspect, the present invention is preferably configured such that the cassette tray has a substantially rectangular tray shape when viewed from above. According to the fifth aspect, it is possible to reliably arrange, on the cassette tray, the cassette which can accommodate an imaging material. According to the sixth aspect, the present invention is preferably configured such that a pair of grip portions each having a substantially concave shape are provided on side surfaces of two end portions of the cassette tray in a substantially length direction when viewed from above. According to the sixth aspect, it is possible to relatively accurately and relatively readily load/unload the cassette tray to/from the cassette tray accommodation space.

According to the seventh aspect, the present invention is preferably configured such that the incubator is an open type incubator. According to the seventh aspect, it is possible to avoid, as much as possible, a situation in which the arrangement and operation of the open type incubator become complicated, by providing at least two tray loading/unloading ports in the cassette tray accommodation space. According to the eighth aspect, the present invention is preferably configured such that the incubator comprises an accessory support strut supported by a main strut supporting the incubator base. According to the eighth aspect, it is possible to easily perform imaging such as X-ray imaging for an infant accommodated in the incubator. According to the ninth aspect, the present invention is preferably configured such that an infrared heater is provided on the accessory support strut. According to the ninth aspect, it is possible to easily keep an infant warm by the infrared heater.

BEST MODE FOR CARRYING OUT THE INVENTION

An embodiment in which the present invention is applied to an open type incubator (a so-called infant warmer) will be described in "1. Overall Schematic Arrangement of Incubator", "2. Arrangements of Movable Wall Portion Structure and Fixed Wall Portion Structure", "3. Arrangement of Cassette Tray Mounting Structure", "4. Operations of Movable Wall Portion Structure and Fixed Wall Portion Structure", and "5. Operation of Cassette Tray Mounting Structure", respectively, with reference to the accompanying drawings.

1. Overall Schematic Arrangement of Incubator

Figure 1:
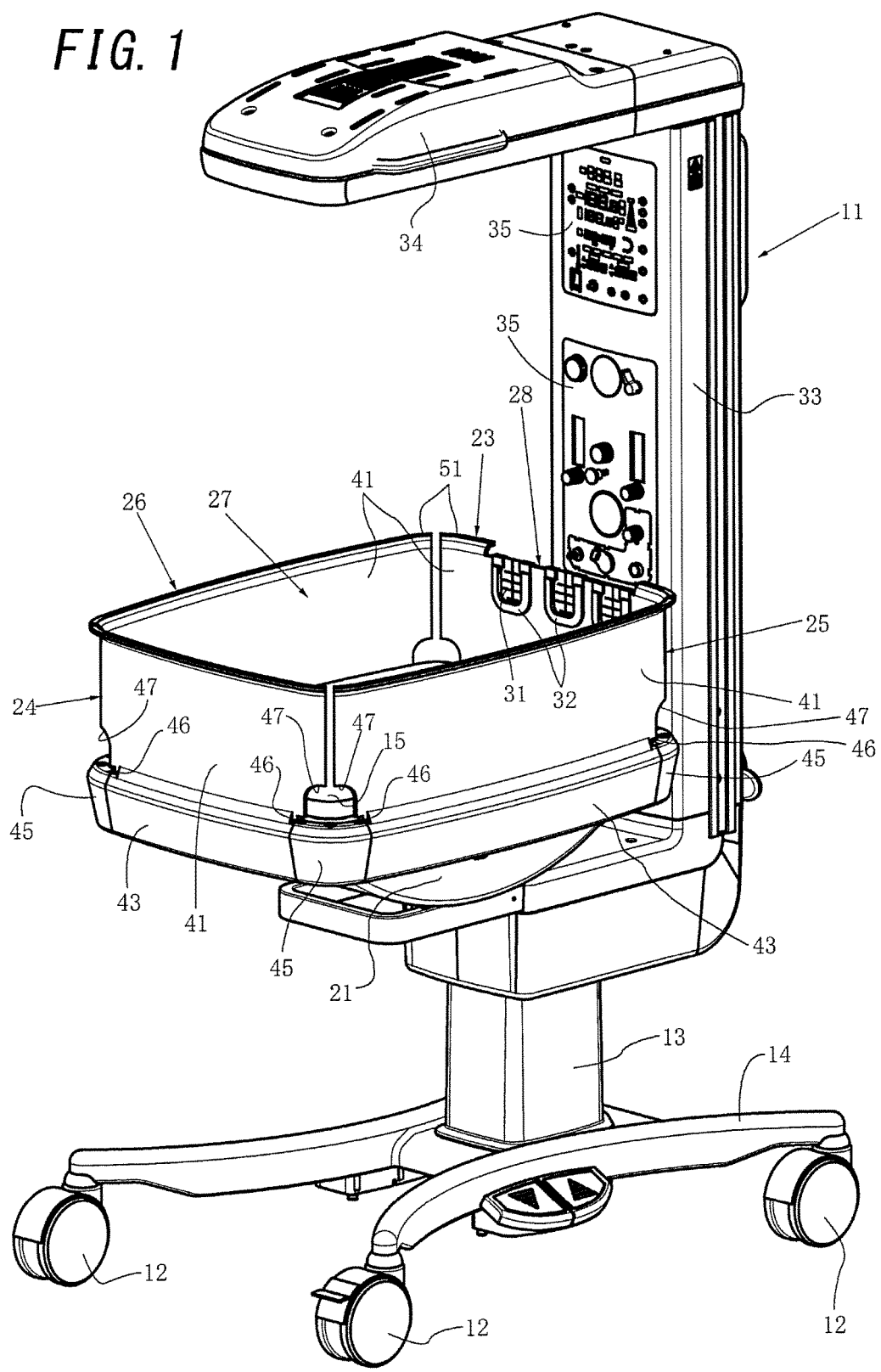
FIG. 1 is a perspective view showing an open type incubator in a normal use state according to an embodiment to which the present invention is applied.
Figure 2:
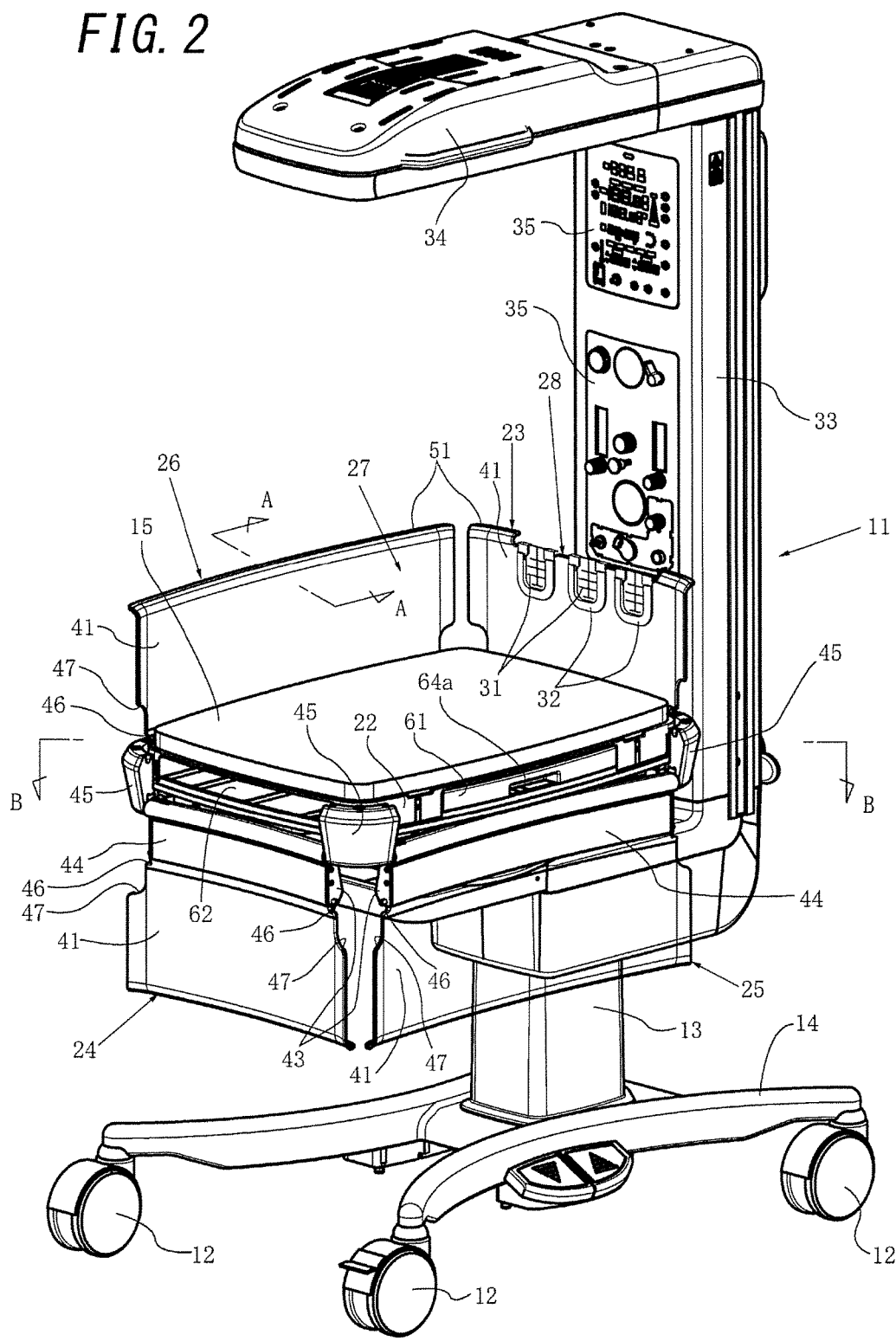
FIG. 2 is a perspective view showing the open type incubator shown in FIG. 1 while movable wall portions in two directions are open.

As shown in FIGS. 1 and 2, an open type incubator 11 includes a carriage 14 to which wheels 12 and a main strut 13 are attached. More specifically, the wheels 12 are attached below the four corners of the carriage 14. The main strut 13 is attached on the carriage 14. An incubator base 21 is provided on the main strut 13. A flat container-shaped bed base (in other words, mattress tray) 22 is provided on the incubator base 21. Note that a mattress 15 on which an infant, for example, a newborn infant, can be laid down can be placed on the bed base 22. The incubator base 21 is provided with a fixed wall portion (so-called fixed baby guard) 23 which is adjacent to an accessory support strut 33 provided on the main strut 13 and generally forms a wall portion on the head side of the infant, a leg-side movable wall portion (so-called movable baby guard) 24 which generally forms a wall portion on the leg side of the infant, a left movable wall portion (so-called movable baby guard) 25 which generally forms a wall portion on the left side of the infant, and a right movable wall portion (so-called movable baby guard) 26 which generally forms a wall portion on the right side of the infant. These wall portions are provided in a substantially rectangular shape as a whole when viewed from above.

As shown in FIGS. 1 and 2, an infant accommodation space 27 having a substantially rectangular parallelepiped shape with an open upper surface is constituted by the bed base 22, and the fixed wall portion 23 and movable wall portions 24 to 26, each of which can take a substantially rectangular shape and can be substantially transparent. Therefore, the left movable wall portion 25 and the right movable wall portion 26 can have substantially the same dimensions. The fixed wall portion 23 and the leg-side movable wall portion 24 whose lengths are slightly shorter than those of the movable wall portions 25 and 26, can have substantially the same dimensions except for three, for example, notch-shaped concave portions 28 provided in the upper side portion of the fixed wall portion 23. The movable wall portions 24 to 26 each can pivot forward and backward, about pivot support shafts 18, 19, or 20 (see FIG. 4) on the left and right sides or the front and rear sides provided in a region including a lower side and its vicinity in the substantially upward erect position (to be referred to as "the above-described erect position" hereinafter) shown in FIG. 1, between the above-described erect position shown in FIG. 1 and the substantially downward hanging position (to be referred to as "the above-described hanging position" hereinafter) shown in FIG. 2 (note that FIG. 2 shows the movable wall portion 26 in the above-described erect position). Note that each of the fixed wall portion 23 and the movable wall portions 24 to 26 can be formed, substantially as a whole, from a substantially transparent plastic plate which can be formed by plastics molding using plastic such as polycarbonate resin or ABS resin as a material.

As shown in FIG. 1, a proper number (three in the embodiment shown in FIG. 1) of grommet members 32 each having cuts 31 for holding a cable can be attached to the notch-shaped concave portions 28 of the fixed wall portion 23. A longitudinal member (not shown) such as an oxygen supply tube can be held in the cuts 31 while extending through the grommet member 32. An infrared heater 34 is provided on the upper end portion of the accessory support strut 33. Various kinds of measurement/control means 35 for body temperature, SpO$_2$, etc. are provided on the accessory support strut 33 so as to be substantially located between the infrared heater 34 and the infant accommodation space 27 when viewed from the front. More specifically, a body temperature control means of the measurement/control means 35 is configured to display a body temperature by receiving a signal from a body temperature probe which measures the body temperature of an infant, and control, for example, the heating temperature of the infrared heater 34. Note that SpO$_2$ indicates a measurement value obtained by measuring the oxygen (that is, O$_2$) saturation of blood (in other words, blood carried from the heart to the whole body) in the artery of the infant or the like using a pulse oximeter.

Figure 3:
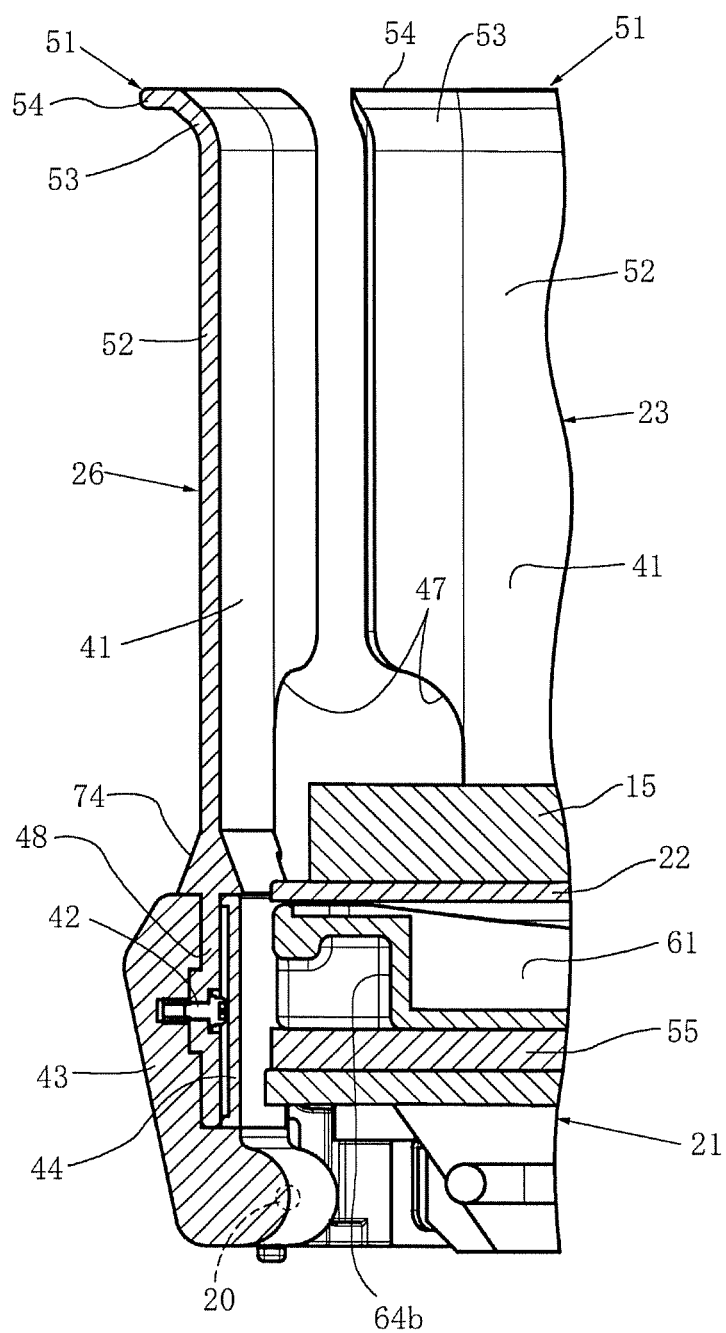
FIG. 3 is a partial sectional view taken along a line A-A in FIG. 2.
Figure 6:
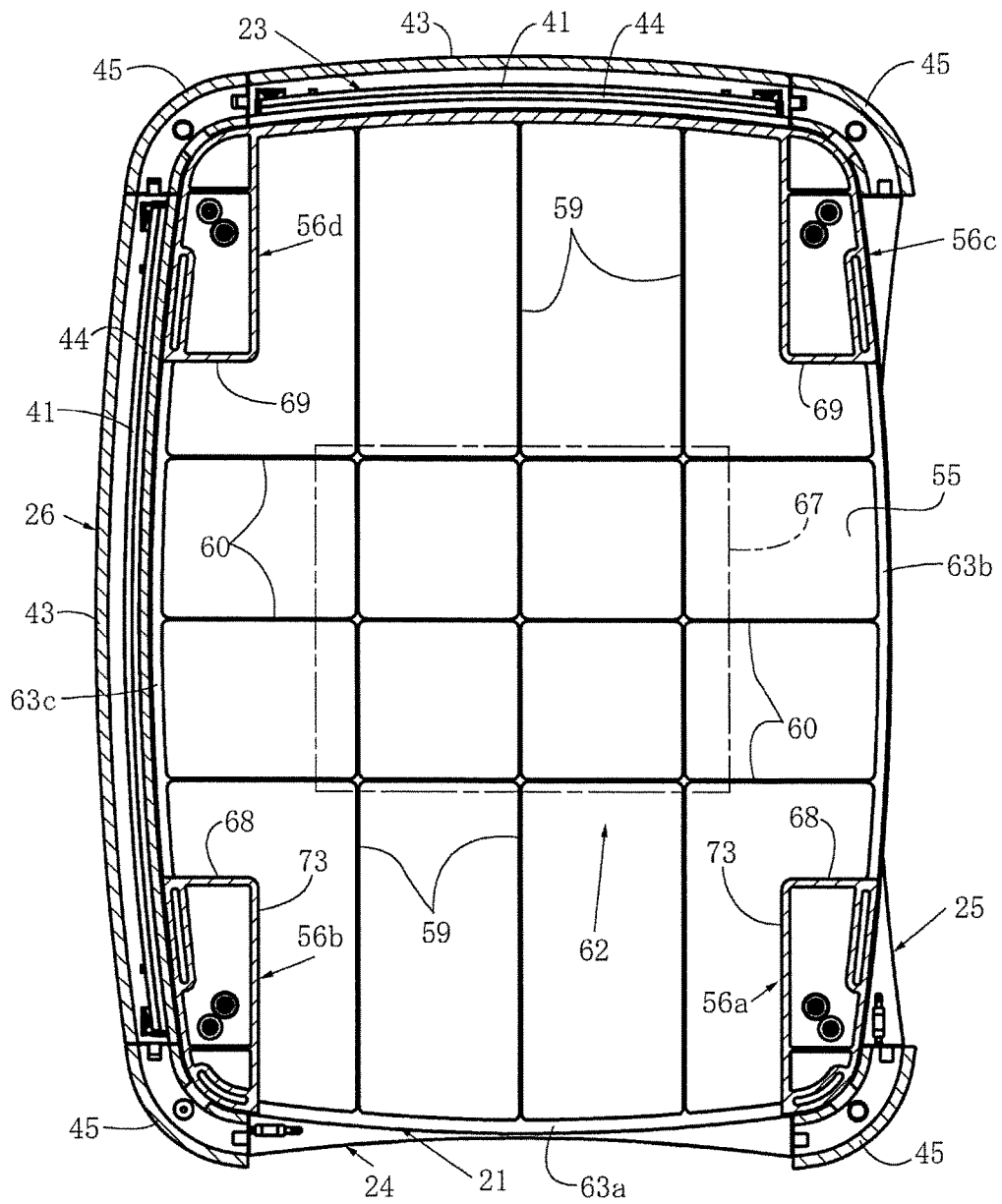
FIG. 6 is a partial sectional view taken along a line B-B shown in FIG. 2.

2. Arrangements of Movable Wall Portion Structure and Fixed Wall Portion Structure As shown in FIGS. 1 to 3, each of the movable wall portions 24 to 26 and the fixed wall portion 23 includes a wall portion main body 41, and a supporting member 43 to which a substantially lower end portion 48 of the wall portion main body 41 is screwed and fixed by screws 42. The substantially entire inside surface of the substantially lower end portion 48 of each wall portion main body 41 is covered by a cover member 44. As shown in FIGS. 1 and 6 and the like, each of the movable wall portions 24 to 26 is pivotably attached to attachment members 45 by the pair of pivot support shafts 18, 19, or 20 in regions including the left and right sides or front and rear sides of the lower end portion of the supporting member 43 of the movable wall portion 24, 25, or 26, and their vicinities. Note that the attachment members 45 are attached and fixed to the substantially four corners of the incubator base 21.

As shown in FIGS. 2 and 6 and the like, the fixed wall portion 23 is attached and fixed to the attachment members 45 on the left and right sides of the fixed wall portion 23 by a pair of left and right coupling members (these coupling members are not shown but correspond to the pivot support shafts 18, 19, or 20) in regions including the left and right sides of the lower end portion of the supporting member 43, and their vicinities. The pair of left and right coupling members are detachably engaged with the engaged portions (not shown) of the attachment members 45 provided on the left and right sides of the fixed wall portion 23. As shown in FIGS. 1 and 3 and the like, a portion, adjacent to the upper surface of the supporting member 43 from substantially above, of the wall portion main body 41 of each of the movable wall portions 24 to 26 and fixed wall portion 23 is formed as a thick portion 74 whose longitudinal section has a substantially triangular shape. Furthermore, the thick portion 74 is provided along the substantially full length in the substantially horizontal direction (in other words, the substantially length direction) of each of the wall portions 23 to 26. Therefore, to prevent dirty water, dust, or the like from entering between the lower end portion 48 and the supporting member 43 or between the lower end portion 48 and the cover member 44, one side portion of the lower end surface on each of the two sides of the thick portion 74 in the thickness direction abuts against the substantially upper surface of the supporting member 43 and the other side portion of the lower end surface abuts against the substantially upper surface of the cover member 44.

As shown in FIGS. 1 and 2 and the like, the fixed wall portion 23 can have substantially the same shape as that of the leg-side movable wall portion 24 except that the fixed wall portion 23 includes the notch-shaped concave portions 28 and grommet members 32. The left movable wall portion 25 can have substantially the same shape as that of the movable wall portion 26. Note that to form recess portions for the four attachment members 45, notched portions 46 are formed in portions corresponding to the attachment members 45 in the two end portions of each of the supporting members 43 of the wall portions 23 to 26. Therefore, the length of each supporting member 43 in the substantially horizontal direction is slightly shorter than that of a corresponding one of the wall portions 23 to 26 in the substantially horizontal direction. A notched portion 47 connecting to each notched portion 46 is formed in a region including the lower end portion on each of the left and right sides or front and rear sides and its vicinity while the wall portion main bodies 41 of the wall portions 23 to 26 are in the above-described erect position.

Figure 4:
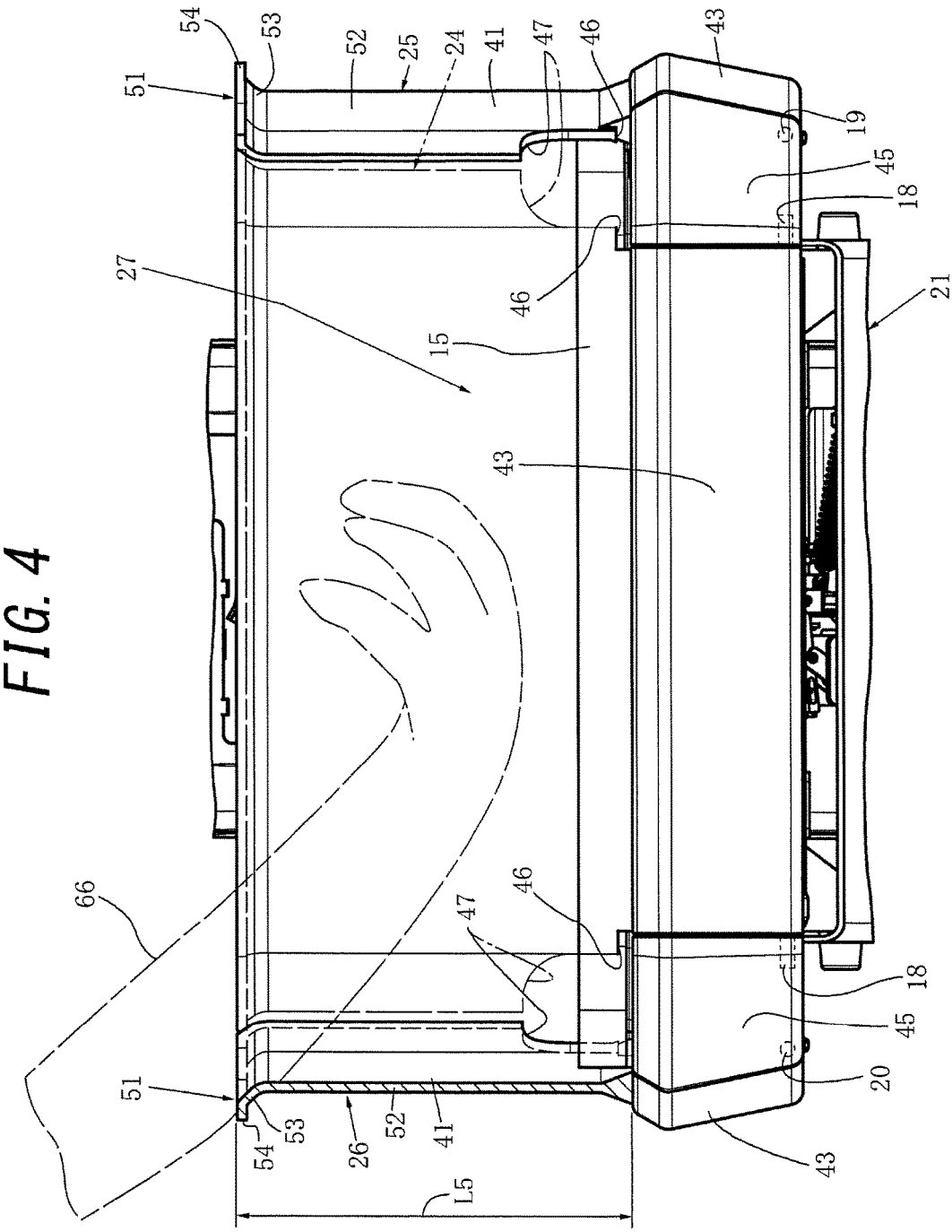
FIG. 4 is a partial front view showing the open type incubator shown in FIG. 1 by partially, longitudinally cutting the movable wall portion.
Figure 5:
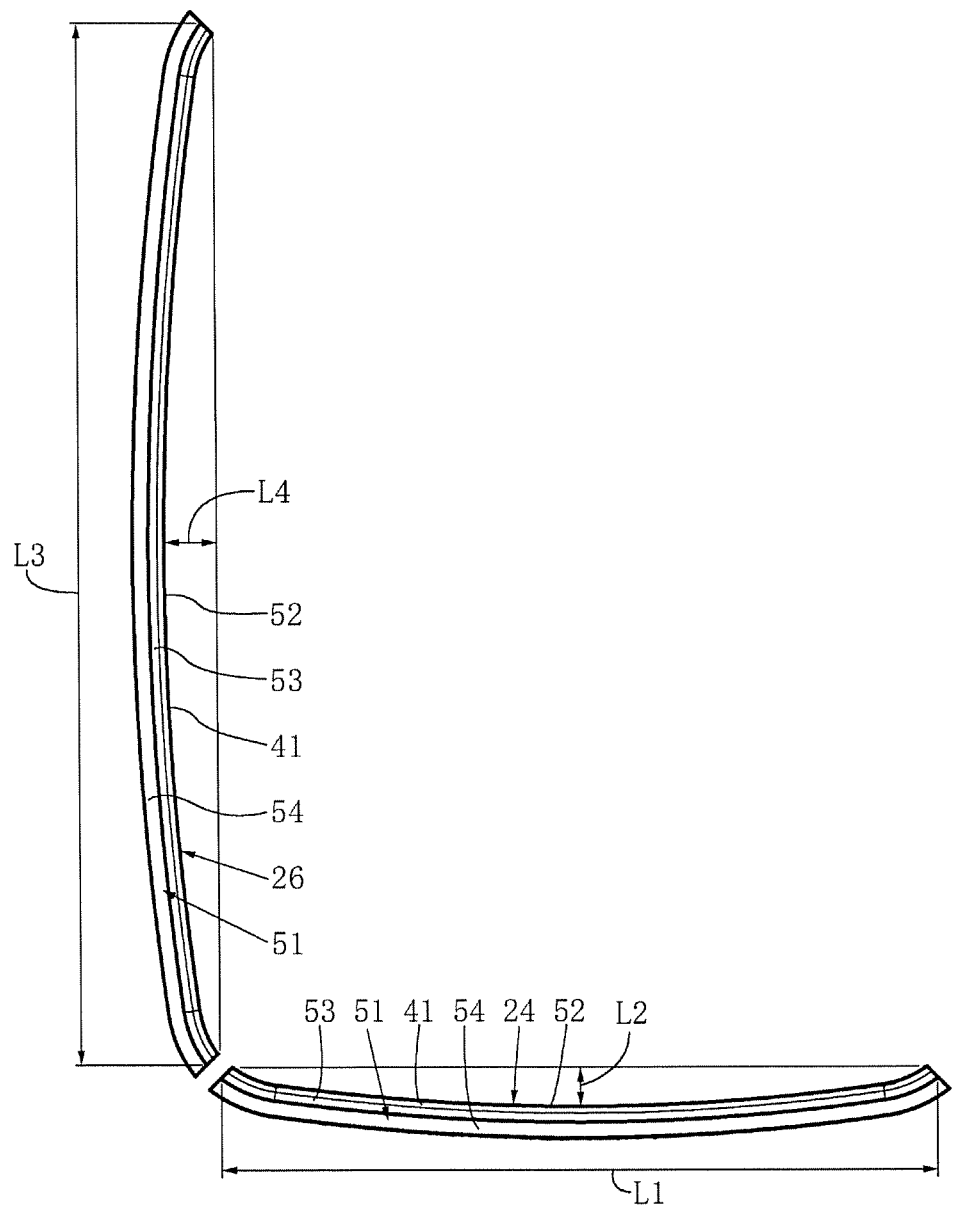
FIG. 5 is a plan view showing movable wall portions in two directions shown in FIG. 1.

As shown in FIGS. 5 and 6 and the like, each of the movable wall portions 24 to 26 and fixed wall portion 23 slightly swells in an arc shape from the inside to the outside when viewed substantially from above. More specifically, a horizontal length L1 between the substantially left and right ends of each of the leg-side movable wall portion 24 and fixed wall portion 23 is about 450 mm when viewed substantially from above. A length L2 in the substantially back-and-forth direction of the inside surface of each of the leg-side movable wall portion 24 and fixed wall portion 23 is about 25 mm when viewed substantially from above. A length L3 between the substantially front and rear ends of each of the movable wall portions 25 and 26 on the left and right sides is about 660 mm. A length L4 in the substantially right-and-left direction of the inside surface of each of the movable wall portions 25 and 26 on the left and right sides is about 34 mm when viewed substantially from above. A length L5 (see FIG. 4) in the substantially vertical direction of a portion, protruding substantially upward from the supporting member 43, of the wall portion main body 41 of each of the wall portions 23 to 26 in the above-described erect position is about 210 mm. Note that the lower end of the length L5 can be at a height substantially coinciding with the lower surface of the bed base 22, at a height substantially coinciding with the upper surface of the bed base 22, or at a height substantially coinciding with a substantially middle portion between the lower surface and the upper surface.

As shown in FIGS. 3 and 5 and the like, in a region including the upper end portion of the wall portion main body 41 of each of the movable wall portions 24 to 26 and fixed wall portion 23 (except for the notch-shaped concave portions 28) in the above-described erect position, and its vicinity, a bent portion 51 is integrally formed in the wall portion main body 41 as part of the wall portion main body 41. Each bent portion 51 includes an inclined portion 53 integrally formed at the upper end of an substantially erect portion (to be referred to as an "erect portion" hereinafter) 52 of the wall portion main body 41 in the above-described erect position, and a substantially horizontal portion (to be referred to as a "horizontal portion" hereinafter) 54 integrally formed on the upper end side of the inclined portion 53 so as to be in a substantially horizontal position in the above-described erect position. Note that the inclined portion 53 can be inclined from the substantially lower side to the substantially upper side at a substantial angle of 45° from the inside surface to the outside surface of the erect portion 52 in the above-described erect position. Furthermore, the horizontal portion 54 can substantially horizontally extend from the upper end of the inclined portion 53 to the outside in the above-described erect position. Referring to FIG. 3, a boundary between the inside surface of the erect portion 52 and the inside surface of the inclined portion 53 is rounded to have a radius of about 14 mm. A boundary between the inside surface of the inclined portion 53 and the upper surface of the horizontal portion 54 is rounded to have a radius of about 2 mm. In addition, the upper and lower ends of the distal end portion of the horizontal portion 54 are each rounded to have a radius of about 2 mm. Therefore, a portion from the inside surface in a region including the upper end portion of the erect portion 52 and its vicinity to the lower surface of the horizontal portion 54 through the inclined surface on the upper side (that is, inside) of the inclined portion 53 and the upper surface of the horizontal portion 54 is a continuous curved surface without any corners.

3. Arrangement of Cassette Tray Mounting Structure

As shown in FIGS. 2, 3, and 6 and the like, the incubator base 21 includes an upper-side support plate portion 55 as a tray support means. On upper surfaces at the substantially four corners of the upper-side support plate portion 55, four strut portions 56a to 56d for attaching and fixing the bed base 22 are provided integrally or individually with the upper-side support plate portion 55. The four attachment members 45 are attached and fixed to the substantially four corners of the incubator base 21, respectively. Furthermore, the bed base 22 is attached and fixed on the four strut portions 56a to 56d. Consequently, a tray accommodation space 62 capable of accommodating a cassette tray 61 is formed between the bed base 22 and the upper-side support plate portion 55. The tray accommodation space 62 includes a leg-side tray loading/unloading port (in other words, a front tray loading/unloading port) 63a, a left tray loading/unloading port 63b, and a right tray loading/unloading port 63c. Note that the leg-side tray loading/unloading port 63a is formed by a space existing between the strut portions 56a and 56b. The left tray loading/unloading port 63b is formed by a space existing between the strut portions 56a and 56c. The right tray loading/unloading port 63c is formed by a space existing between the strut portions 56b and 56d. Note that as shown in FIG. 6 and the like, on the upper-side support plate portion 55, three grooves 59 extending along the full length in the substantially back-and-forth direction and three grooves 60 extending along the full length in the substantially right-and-left direction are formed to improve the moldability of the upper-side support plate portion 55 formed by plastics molding using plastic such as polypropylene resin or ABS resin as a material, and to prevent deformation of the upper-side support plate portion 55.

Figure 7:
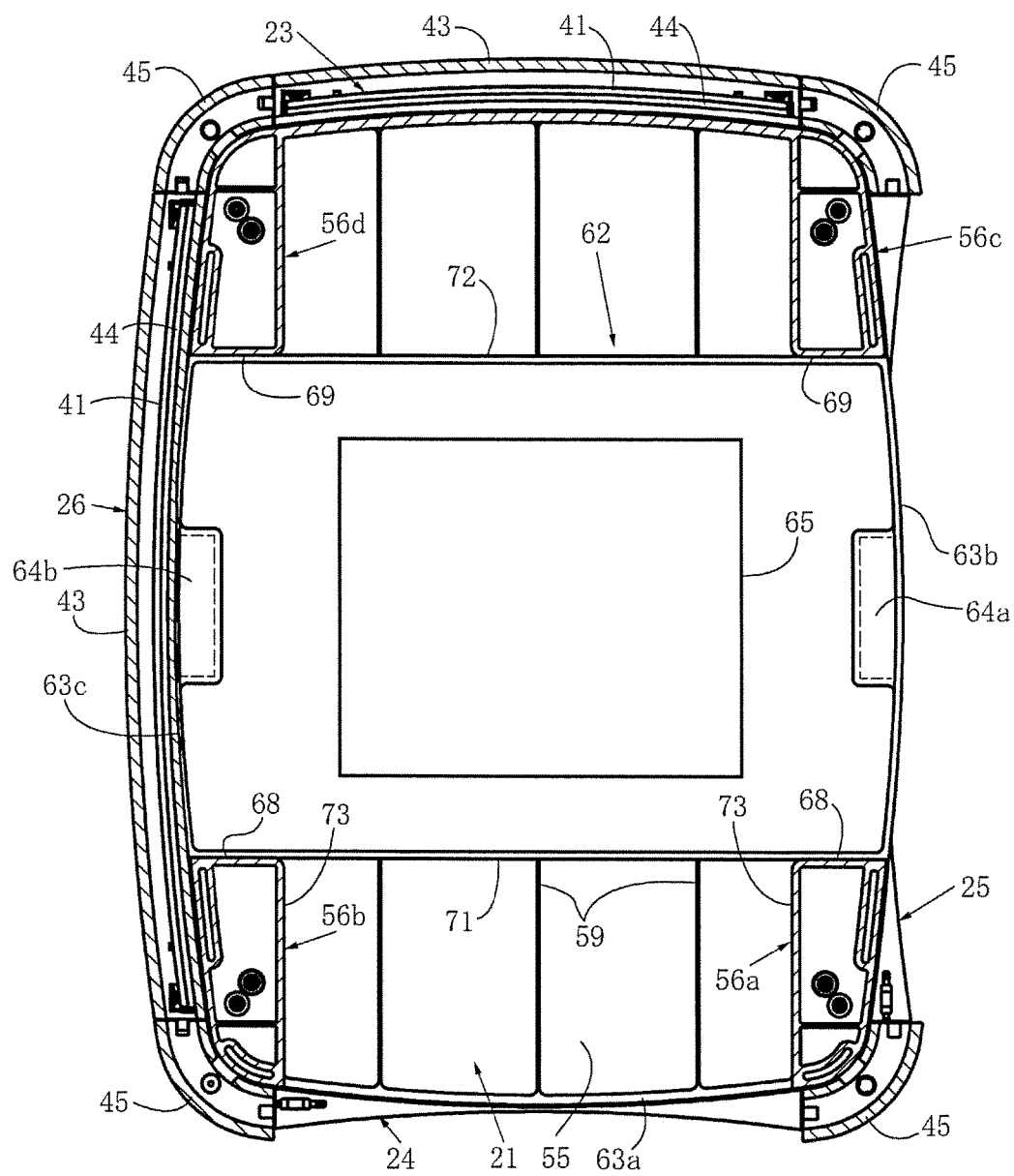
FIG. 7 is a sectional view similar to that of FIG. 6 while an X-ray tray is mounted from the first direction.
Figure 8:
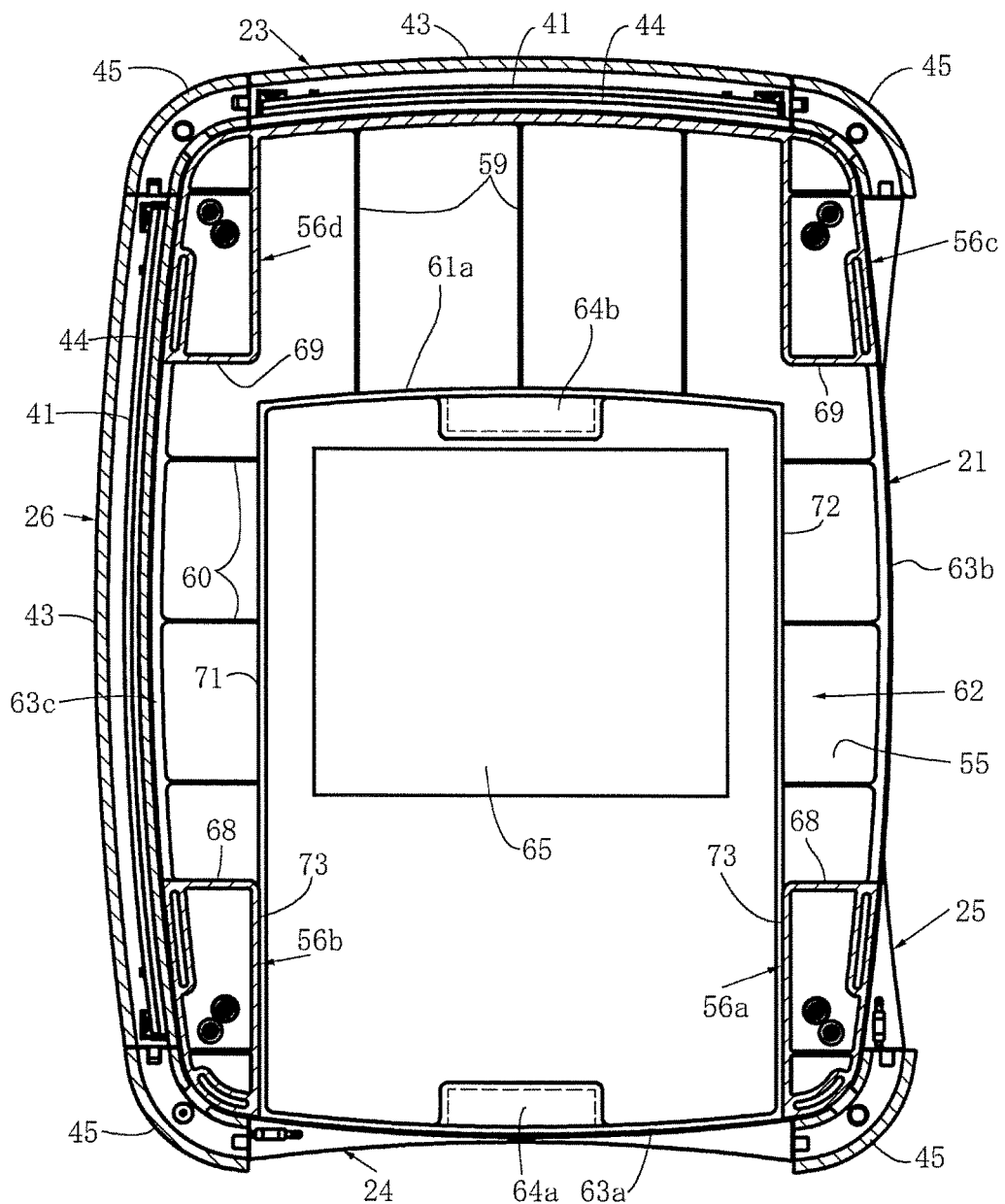
FIG. 8 is a sectional view similar to that of FIG. 6 while the X-ray tray is mounted from the second direction.

As shown in FIGS. 2, 7, and 8 and the like, the cassette tray 61 can have a substantially rectangular tray shape when viewed from above. On the side surfaces of the two end portions of the cassette tray 61 in the substantially length direction when viewed from above, a pair of grip portions 64a and 64b each having a substantially concave shape are provided. A cassette 65 that can accommodate imaging materials such as an imaging film and CCD image sensor (that is, an image sensor using a charge coupled device) which can be used for X-ray imaging or the like is arranged on the cassette tray 61. The width of the cassette tray 61 can be substantially equal to the interval between the strut portions 56a and 56c (in other words, the interval between the strut portions 56b and 56d) or slightly smaller than the interval. Alternatively, the width of the cassette tray 61 can be substantially equal to the interval between the strut portions 56a and 56b or slightly smaller than the interval. The interval between the strut portions 56a and 56c, that between the strut portions 56b and 56d, and that between the strut portions 56a and 56b can be substantially equal to each other.

4. Operations of Movable Wall Portion Structure and Fixed Wall Portion Structure As shown in FIGS. 2 and 6 and the like, the fixed wall portion 23 is stationarily held in the above-described erect position when it is detachably attached and fixed to the pair of left and right attachment members 45 fixed to the incubator base 21 on the left and right sides of the fixed wall portion 23. To the contrary, when each of the leg-side movable wall portion 24 and the left and right movable wall portions 25 and 26 pivots forward from the above-described erect position shown in FIG. 1 to the above-described hanging position exemplified in FIG. 2 with respect to the movable wall portions 24 and 25, the lock by a lock means (not shown) which locks the forward pivoting movement of each of the movable wall portions 24 to 26 is released. The operator can then make each of the movable wall portions 24 to 26 pivot forward from the above-described erect position to the above-described hanging position by making each of the movable wall portions 24 to 26 pivot forward about the corresponding pair of pivot support shafts 18, 19, or 20, as needed. Note that the forward pivoting movement of each of the movable wall portions 24 to 26 can be performed at low speed by the damper function of a damper (not shown) capable of suppressing the pivoting speed of the forward pivoting movement. To make each of the movable wall portions 24 to 26 pivot backward from the above-described hanging position to the above-described erect position, the operator need only manually make each of the movable wall portions 24 to 26 pivot backward about the corresponding pair of pivot support shafts 18, 19, or 20 of the movable wall portion 24, 25, or 26.

When the operator lays an infant, for example, a newborn infant down on the mattress 15 of the open type incubator 11 or holds up the infant from the mattress 15, he/she inserts his/her arm 66 to the infant accommodation space 27, as shown in FIG. 4. In this case, the arm 66 of the operator can abut against the upper end portions of the movable wall portions 24 to 26 and fixed wall portion 23, as shown in FIG. 4. However, the upper end portion of each of the movable wall portions 24 to 26 forms the bent portion 51 while the upper end portion of the fixed wall portion 23 except for the notch-shaped concave portions 28 forms the bent portion 51. The inclined portion 53 and the horizontal portion 54 are sequentially, continuously formed at the upper end of the erect portion 52 in the bent portion 51, as shown in FIG. 3. In addition, joints between the inside surface of the erect portion 52, the upper surface of the inclined portion 53, and the upper surface of the horizontal portion 54, and the distal end portion of the upper surface of the horizontal portion 54 are rounded. Therefore, even if the arm 66 of the operator abuts against the upper end portion (especially, the horizontal portion thereof) of the wall portion main body 41 relatively hard, there is no risk that the operator feels a pain or the arm 66 gets hurt. In addition, each of the movable wall portions 24 to 26 and fixed wall portion 23 slightly swells in an arc shape from the inside to the outside when viewed substantially from above, as shown in FIGS. 5 and 6 and the like. Therefore, each of the movable wall portions 24 to 26 and fixed wall portion 23 can have a sufficient strength as the external wall portion of the infant accommodation space 27 of the open type incubator 11 in combination with the wall portion main body 41 including the bent portion 51.

5. Operation of Cassette Tray Mounting Structure

To store the cassette tray 61 in the cassette tray accommodation space 62 of the open type incubator 11, it is only necessary to insert the cassette tray 61 toward the cassette tray accommodation space 62 from one of the three tray loading/unloading ports 63a to 63c. In this case, when the operator inserts the cassette tray 61 from the tray loading/unloading port 63b to the tray accommodation space 62, he/she makes the left movable wall portion 25 pivot forward from the above-described erect position to the above-described hanging position, as shown in FIGS. 2 and 6 and the like. Subsequently, the operator grips the grip portion 64a and the like by the hands and the like, and makes the cassette tray 61 slide on the upper-side support plate portion 55 of the incubator base 21, thereby inserting the cassette tray 61 to the cassette tray accommodation space 62. In this case, the operator inserts the cassette tray 61 to the cassette tray accommodation space 62 along the substantially longitudinal direction of the cassette tray 61 from a side of the cassette tray 61 on which one of the pair of front and rear grip portions 64a and 64b is provided. At this time, each of a set of rear surfaces 68 of the strut portions 56a and 56b and a set of front surfaces 69 of the strut portions 56c and 56d serves as a position holding portion serving also as a guide portion, and abuts against a corresponding one of the side wall portions 71 and 72 on the long wall sides of the cassette tray 61. As a result, the cassette tray 61 is arranged symmetrically in the right-and-left direction in the cassette tray accommodation space 62 in FIG. 7, as shown in FIGS. 2 and 7 and the like.

When the operator takes out the cassette tray 61, which is accommodated in the cassette tray accommodation space 62 as shown in FIG. 7, from the cassette tray accommodation space 62, he/she grips the grip portion 64a or 64b by the hand or the like, and makes the cassette tray 61 slide on the upper-side support plate portion 55, thereby pulling out the cassette tray 61 to the right or left side in FIG. 7 along the substantially longitudinal direction of the cassette tray 61. In this case as well, each of the set of rear surfaces 68 of the strut portions 56a and 56b and the set of front surfaces 69 of the strut portions 56c and 56d serves as a guide portion to guide a corresponding one of the side wall portions 71 and 72 on the long wall sides of the cassette tray 61. Note that a rectangle 67 indicated by chain lines indicates an estimated cassette mounting position in FIG. 6. Referring to FIGS. 7 and 8, the cassette 65 is arranged at substantially the same position as that of the rectangle 67 when viewed from above.

When the operator inserts the cassette tray 61 to the cassette tray accommodation space 62 from the tray loading/unloading port 63c, he/she need only perform substantially the same operation except that the cassette tray 61 is inserted from the tray loading/unloading port 63b to be symmetrical in the right-and-left direction, as described above, and a detailed description thereof will be omitted. Furthermore, when the operator takes out, from the cassette tray accommodation space 62, the cassette tray 61 accommodated in the cassette tray accommodation space 62, he/she grips the grip portion 64a or 64b by the hand, and makes the cassette tray 61 slide on the upper-side support plate portion 55, thereby relatively correctly and relatively readily pulling out the cassette tray 61 to the right or left side (in other words, the side convenient for the operator at this time) in FIG. 7. With respect to this point, it is possible to relatively readily insert the cassette tray 61 to the cassette tray accommodation space 62 by performing the inverse operation of the operation performed when pulling out the cassette tray 61.

When the operator inserts the cassette tray 61 from the tray loading/unloading port 63a to the cassette tray accommodation space 62 or takes out the cassette tray 61 in the cassette tray accommodation space 62 from the tray loading/unloading port 63a, it is only necessary to perform the following operation, as compared with a case in which the cassette tray 61 is inserted or taken out from the tray loading/unloading port 63b. That is, the operator first moves in advance the cassette 65 toward an insertion end 61a of the cassette tray 61, as shown in FIG. 8. To do this, on the upper surface or the like of the cassette tray 61, an instruction line, an instruction groove, an instruction concave portion, or the like for arranging the cassette 65 at the substantially center position on the upper surface of the cassette tray 61, as shown in FIG. 7, can be formed in advance. Furthermore, on the upper surface or the like of the cassette tray 61, an instruction line, an instruction groove, an instruction concave portion, or the like for arranging the cassette 65 at a position near one end of the upper surface of the cassette tray 61 in the length direction, as shown in FIG. 8, can be formed in advance. Subsequently, as shown in FIGS. 2 and 8 and the like, the operator makes the leg-side movable wall portion 24 pivot forward from the above-described erect position to the above-described hanging position. The operator inserts the cassette tray 61 to the cassette tray accommodation space 62 from the tray loading/unloading port 63a along the substantially longitudinal direction of the cassette tray 61, similarly to the above-described case in which the operator inserts the cassette tray 61 to the cassette tray accommodation space 62 from the tray loading/unloading port 63b. At this time, the inside surface 73 of each of the strut portions 56a and 56b serves as a position holding portion serving also as a guide portion, and abuts against a corresponding one of the side wall portions 72 and 71 on the long wall sides of the cassette tray 61.

When the operator takes out the cassette tray 61, which is accommodated in the cassette tray accommodation space 62 as shown in FIG. 8, from the cassette tray accommodation space 62, he/she grips the grip portion 64a by the hand or the like, and makes the cassette tray 61 slide on the upper-side support plate portion 55, thereby pulling out the cassette tray 61 along the substantially longitudinal direction of the cassette tray 61 downward in FIG. 8. In this case as well, the inside surface 73 of the strut portions 56a and 56b serve as guide portions to guide the side wall portions 72 and 71 on the long wall sides of the cassette tray 61, respectively.

Having described a specific preferred embodiment of the present invention with reference to the accompanying drawings, it is to be understood that the present invention is not limited to the precise embodiment, and that various changes and modifications may be effected therein by one skilled in the art without departing from the scope or spirit of the invention as defined in the appended claims.

For example, in the above-described embodiment, the present invention is applied to the open type incubator. However, the present invention is applicable to not only the open type incubator but also a closed type incubator or an open type incubator serving also as a closed type incubator. In this case, for example, three relatively horizontally long open/close doors which can be opened/closed, similarly to the above-described movable wall portions 24 to 26, when storing or taking out the cassette tray 61 in or from the cassette tray accommodation space 62, can be provided on the incubator base 21 for the cassette tray accommodation space 62.

In the above-described embodiment, the cassette tray accommodation space 62 includes three of the front tray loading/unloading port 63a, the rear tray loading/unloading port, the left tray loading/unloading port 63b, and the right tray loading/unloading port 63c. However, the cassette tray accommodation space 62 may include two tray loading/unloading ports (for example, the left tray loading/unloading port 63b and right tray loading/unloading port 63c, one of the front tray loading/unloading port 63a and the rear tray loading/unloading port and one of the left and right tray loading/unloading ports 63b and 63c, or the front tray loading/unloading port 63a and the rear tray loading/unloading port). Furthermore, even if the cassette tray accommodation space 62 includes three tray loading/unloading ports, the front tray loading/unloading port 63a, the rear tray loading/unloading port, and the left or right tray loading/unloading port 63b or 63c may be included. The cassette tray accommodation space 62 can also include four tray loading/unloading ports (that is, front, rear, left, and right tray loading/unloading ports).

INDUSTRIAL APPLICABILITY

The present invention can be used for the manufacture or the like of an incubator, for example, an open type incubator, an open type incubator serving also as a closed type incubator, or a closed type incubator, capable of readily storing or taking out a cassette tray in or from a cassette tray accommodation space through the second or first tray loading/unloading port even if a doctor or nurse performs an operation in a region including the first or second tray loading/unloading port and its vicinity in a region including the cassette tray accommodation space and its vicinity or even if a sophisticated article such as a sophisticated medical apparatus exists in the region including the first or second tray loading/unloading port and its vicinity in the region including the cassette tray accommodation space and its vicinity.

The invention claimed is:

1. An incubator comprising:
an incubator base that is provided on a main strut;
a bed base that is provided on the incubator base and on which a mattress is placed; and
a cassette tray accommodation space which is formed between the incubator base and the bed base, wherein the cassette tray accommodation space comprises at least three tray loading/unloading ports selected from: a front tray loading/unloading port, a rear tray loading/unloading port, a left tray loading/unloading port, and a right tray loading/unloading port.

2. The incubator of claim 1, further comprising a rear baby guard, a movable front baby guard, a movable left baby guard, and a movable right baby guard, wherein:
one end portion of each of the movable baby guards is pivotably attached to the incubator base;
the tray loading/unloading ports are closed by the movable baby guards, respectively, in a backward pivoting state in which each of the movable baby guards is in a substantially erect position; and
the tray loading/unloading ports are opened when each of the movable baby guards pivots forward in a substantially hanging direction.

3. The incubator of claim 1, wherein the cassette tray accommodation space comprises the front tray loading/unloading port, the left tray loading/unloading port, and the right tray loading/unloading port.

4. The incubator of claim 1, further comprising:
a cassette tray;
a front left first strut portion, a front right second strut portion, a rear left third strut portion, and a rear right fourth strut portion, wherein:
the second strut portions and/or the third and said fourth strut portions function to hold and guide the cassette tray when the cassette tray is inserted into the cassette tray accommodation space in a back-and-forth direction, and
the first and third strut portions and/or the second and fourth strut portions function to hold and guide the cassette tray when the cassette tray is inserted into the cassette tray accommodation space in a right-and-left direction.

5. The incubator of claim 4, wherein a width of the cassette tray is substantially equal to each of a distance between: (a) the first strut portion and the second strut portion, (b) the first strut portion and the third strut portion, and (c) the second strut portion and the fourth strut portion.

6. The incubator of claim 1, wherein the cassette tray accommodation space is configured to accommodate a cassette tray, the cassette tray comprising a substantially rectangular tray shape when viewed front above.

7. The incubator of claim 1, wherein the cassette tray accommodation space is configured to accommodate a cassette tray, the cassette tray comprising a pair of grip portions, each having a substantially concave shape, and which are located on side surfaces of two end portions of the cassette tray in a substantially lengthwise direction when viewed front above.

8. The incubator of claim 1, wherein the incubator is an open type incubator.

9. The incubator of claim 1, further comprising an accessory support strut supported by the main strut supporting the incubator base.

10. The incubator of claim 9, wherein an infrared heater is provided on the accessory support strut.

* * * * *